(12) United States Patent
Vadrevu et al.

(10) Patent No.: US 10,568,957 B2
(45) Date of Patent: Feb. 25, 2020

(54) ROTAVIRUS VACCINE COMPOSITIONS AND PROCESS FOR PREPARING THE SAME

(71) Applicants: Bharat Biotech International Limited, Hyderabad (IN); Krishna Mohan Vadrevu, Hyderabad (IN); Sai Devarajulu Prasad, Hyderabad (IN)

(72) Inventors: Krishna Mohan Vadrevu, Hyderabad (IN); Sai Devarajulu Prasad, Hyderabad (IN)

(73) Assignee: Bharat Biotech International Ltd., Hyderabad (IN)

( * ) Notice: Subject to any disclaimer, the term of this patent is extended or adjusted under 35 U.S.C. 154(b) by 0 days.

(21) Appl. No.: 14/396,691

(22) PCT Filed: Apr. 23, 2013

(86) PCT No.: PCT/IN2013/000272
§ 371 (c)(1),
(2) Date: Oct. 23, 2014

(87) PCT Pub. No.: WO2013/160913
PCT Pub. Date: Oct. 31, 2013

(65) Prior Publication Data
US 2015/0098967 A1  Apr. 9, 2015

(30) Foreign Application Priority Data
Apr. 23, 2012 (IN) .............................. 667/CHE/2012

(51) Int. Cl.
*A61K 39/15* (2006.01)
*A61K 39/39* (2006.01)
(Continued)

(52) U.S. Cl.
CPC ................ *A61K 39/39* (2013.01); *A61K 9/08* (2013.01); *A61K 39/12* (2013.01); *A61K 39/15* (2013.01);
(Continued)

(58) Field of Classification Search
None
See application file for complete search history.

(56) References Cited

U.S. PATENT DOCUMENTS 5,914,135 A * 6/1999 Dubek ................. A61K 9/0095
424/601
6,616,931 B1 * 9/2003 Burke .................... A61K 39/15
424/215.1
(Continued)

FOREIGN PATENT DOCUMENTS

| WO | WO 2006/087205 | 8/2006 |
| WO | WO 2007/132480 A2 | 11/2007 |
| WO | WO 2009/042202 A2 | 4/2009 |

OTHER PUBLICATIONS

Dennison, "A Simple and Universal Method for Making up Buffer Solutions," Biochemical Education 16(4): 210-211 (1988).*
(Continued)

*Primary Examiner* — M Franco G Salvoza
(74) *Attorney, Agent, or Firm* — Remenick PLLC

(57) ABSTRACT

Invention provides novel rotavirus vaccine compositions comprising rotavirus antigens, stabilizers and buffers. The buffers in the invention are pre-mixed in the rotavirus vaccine compositions to neutralize the high acidic pH of the stomach without requiring separate administration of an antacid before vaccine administration. Vaccine compositions with buffers of the invention are stable liquid rotavirus vaccine formulations for oral administration.

41 Claims, 14 Drawing Sheets

Stability of rotavirus vaccine formulations at 2-8°C with citrate phosphate buffers

(51) Int. Cl.
*A61K 39/12* (2006.01)
*A61K 9/08* (2006.01)
A61K 47/26 (2006.01)
A61K 47/42 (2017.01)
A61K 39/00 (2006.01)

(52) U.S. Cl.
CPC .............. *A61K 47/26* (2013.01); *A61K 47/42* (2013.01); *A61K 2039/55505* (2013.01); *A61K 2039/55511* (2013.01); *C12N 2720/12334* (2013.01)

(56) References Cited

U.S. PATENT DOCUMENTS

| | | | | |
|---|---|---|---|---|
| 2002/0058043 A1* | 5/2002 | Hoshino | ................ | A61K 39/15 424/215.1 |
| 2008/0166372 A1* | 7/2008 | Vande Velde | .......... | A61K 39/15 424/205.1 |
| 2008/0226682 A1* | 9/2008 | Brake | .................. | A61K 9/0095 424/278.1 |
| 2009/0028828 A1* | 1/2009 | Colau | .................... | A61K 39/15 424/93.6 |
| 2010/0226939 A1* | 9/2010 | Truong-Le | ............. | A61K 39/15 424/215.1 |
| 2011/0243988 A1 | 10/2011 | Ohtake | | |
| 2013/0123707 A1* | 5/2013 | Determan | ............ | A61K 9/0021 604/173 |

OTHER PUBLICATIONS

Davis, "Studies of Basic Carbonates", Journal of the Society of Chemical Industry, vol. 25: excerpt of pp. 788-791 (Year: 1906).*
International Search Report issued in connection with International Application No. PCT/IN2013/000272, dated Oct. 10, 2013.

* cited by examiner

Fig 1: Stability of rotavirus vaccine formulations at 2-8°C with citrate phosphate buffers

Stability of ORV 116E Liquid Formulations at 2-8 Deg C

Fig 2: Stability of rotavirus vaccine formulations at 25°C with citrate phosphate buffers

Fig 3: Stability of rotavirus vaccine formulations at 37°C with citrate phosphate buffers

Figure 4: Baby Rossete Rice Assay results of various formulations to study the buffering capacity of the formulations.

Figure 5 : Stability Studies of rotavirus vaccine formulations using Citrate Bicarbonate Buffers at 2°-8°C.

Stability of ORV 116E Liquid Formulations at 25 Deg C

Figure 6 : Stability Studies of rotavirus vaccine formulations using Citrate Bicarbonate Buffers at 25°C.

Figure 7: Stability Studies of rotavirus vaccine formulations using Carbonate Bicarbonate Buffers at 2-8°C.

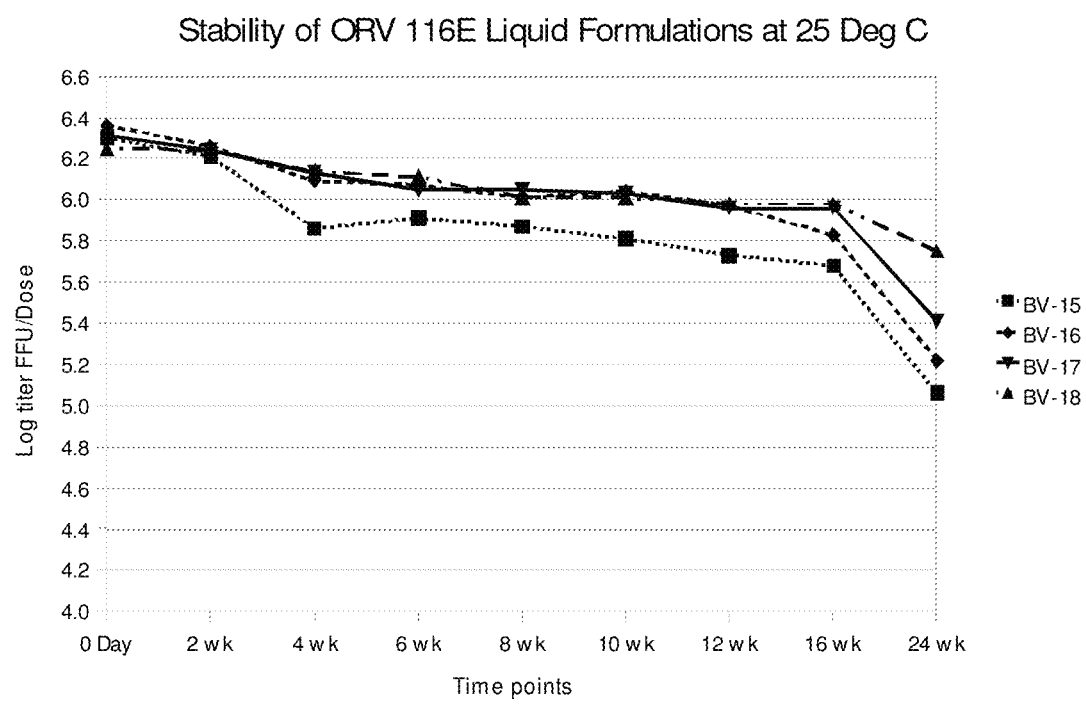
Figure 8: Stability Studies of rotavirus vaccine formulations using Carbonate Bicarbonate Buffers at 25°C.

Stability of ORV 116E Liquid Formulation BV-19 at 25 Deg C and 2-8 Deg C

Figure 9: Stability Studies of rotavirus vaccine formulations using Magnesium Hydroxide Carbonate Buffers at 2-8°C and 25°C.

Figure 10: Stability Studies of rotavirus vaccine formulations using ammonium Based Mixed Buffers at 2-8°C.

Fig.11. Stability of rotavirus vaccine formulations at 25°C with ammonium based Mixed Buffers Fig 12. Stability of rotavirus vaccine formulations at 37°C with ammonium based mixed buffers.

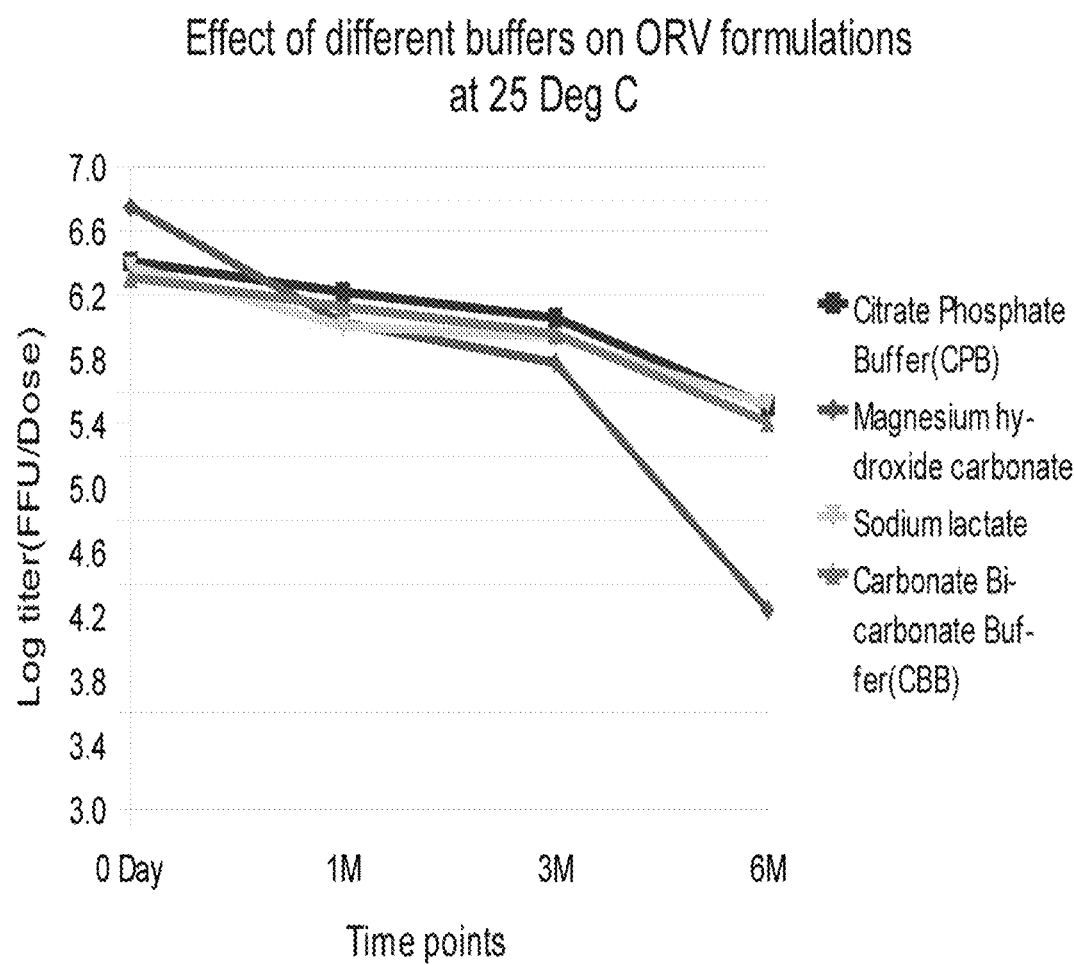
Figure 13: Effect of Different Buffers on ORV formulations on log titer vs. time.

Figure 14: Effect of Different Buffers on ORV formulations on log loss in titer (ffu/dose) vs. time.

ROTAVIRUS VACCINE COMPOSITIONS AND PROCESS FOR PREPARING THE SAME

This application is a national phase application under 35 U.S.C. § 371 of International Application No. PCT/IN2013/000272, filed Apr. 23, 2013, which claims priority to Indian Patent Application No. 667/CHE/2012, filed on Apr. 23, 2012 the disclosures of which are both hereby incorporated by reference.

FIELD OF THE INVENTION

The invention relates to novel rotavirus vaccine compositions and process for preparing the same. More particularly, the invention relates to novel rotavirus vaccine compositions comprising rotavirus antigens, stabilizers and novel buffers. The buffers are pre-mixed in the rotavirus vaccine compositions of the invention. Vaccine compositions of the invention are stable liquid rotavirus vaccine formulations for oral administration.

BACKGROUND OF THE INVENTION

Rotavirus is the most common cause of severe, dehydrating diarrhea worldwide. Every year, over half a million children less than 5 years of age die due to rotavirus diarrhea. More than 80% of these rotavirus-related deaths occur in developing countries of sub-Saharan Africa and South Asia. Moreover, rotavirus is responsible for 25-50% of all diarrheal hospitalizations in both developing and developed countries and 23 million outpatient health care encounters annually in young children. Almost every child by 5 years of age will have been infected with rotavirus. Owing to the tremendous global burden of rotavirus disease, development of vaccines against this pathogen has been a priority for the past three decades. Two live, orally administered rotavirus vaccines available in the market are ROTATEQ® rotavirus vaccine (Merck and Co., Inc., PA, USA and Sanofi Pasteur MSD SNC, Lyon, France) and ROTARIX® rotavirus vaccine (GSK Biologicals, Rixensart, Belgium). In April and October 2009, WHO's Strategic Advisory Group of Experts (SAGE) reviewed additional efficacy data from different populations in Africa and Asia, and post-licensure studies in the America, and extended the recommendation for vaccination to all regions of the world.

The rotavirus capsid is made up of three concentric protein layers. The outer layer, consisting of VP7 and VP4, is lost during virus entry into the host cell. Rotavirus field isolates can be adapted to high-titer growth in tissue culture by treatment with trypsin and by supplementing the culture medium with trypsin, which cleaves VP4 into two fragments, VP8* and VP5*. It is known that protease inhibitors reduce the replication of rotavirus, in vitro and in vivo. When associated with triple-layer particles (TLPs), trypsin is inactive and not accessible to protease inhibitors, such as aprotinin. When the outer layer is solubilized by calcium-chelating agents, VP5*, VP8* and VP7 are released and the associated trypsin is activated, allowing cleavage of the viral capsid proteins, as well as other exogenous proteins. It is shown that addition of trypsin inhibitors significantly reduces synthesis of viral mRNA and viral proteins in cells and has a major inhibitory effect if present when virus enters the cell. This indicates that incorporation of trypsin into rotavirus particles may enhance its infectivity.

The infectivity is enhanced by treatment with trypsin. Trypsin converts a noninfectious fraction of virus into infectious virus by allowing this fraction to un-coat in the infected cell. Trypsin was found to cleave an 88,000-dalton structural polypeptide of bovine rotavirus generating 67,000- and 20,000-dalton cleavage products. Activation of Rotavirus with trypsin (Porcine origin) is established and addition of trypsin in the medium post infection was also done to get optimal yields. However, the source of trypsin is porcine i.e. from pigs. It has been shown that trypsin coming from porcine origin might contain other contaminating viruses like Porcine circovirus 1 and 2 which is not desirable. Traces of other risky pollutants like polychlorinated bi-phenyls (PCBs) can also be found when Porcine trypsin is used for growing rotaviruses. Therefore, it is essential that, trypsin of animal origin to be avoided from bioprocess of rotavirus culture, to the extent possible. Additionally, since porcine related products is also a barrier to certain religious faiths especially in the Islamic regions of the world, therefore, vaccines absolutely free of porcine origins will be more beneficial and useful. Process development studies were initiated to introduce the use of Recombinant trypsin which is novel step in the bioprocess to overcome the risk of PCB and other animal sources in the vaccine formulations. Recombinant trypsin is animal component free (ACF), highly specific in activity, free of contaminating chymotrypsin, free of adventitious agents of animal origin and safe for human consumption.

Wyeth had the earliest privilege to launch a commercial rotavirus vaccine in the market place in 1998-99. The composition of Wyeth's Rotashield included live human-monkey reassortant tetravalent rotavirus antigen, sucrose, monosodium glutamate, potassium monophosphate, potassium diphosphate, fetal-bovine serum, neomycin sulphate, in amphotericin B medium grown in fetal rhesus diploid cell lines. However, due to issues related with intussusception, and associated adverse effects following vaccine administration, Wyeth withdrew its commercial rotavirus vaccine formulations from market. Current vaccines, including one comprising a monovalent human serotype—P1A[8]G1 (Rotarix), and another comprising five human-bovine reassortants—G1, G2, G3, G4 and P1A[8] (RotaTeq), have demonstrated general efficacy and safety in clinical trials. Although considerable progress has been made with the association of intussusception with rotavirus vaccines, major unanswered questions still remain to be solved. It has been already observed and proved that available rotavirus vaccines generally have yielded poor efficacy when tested in developing countries which has led to concerns about the potential effectiveness of any future live oral rotavirus vaccine in these settings. (Bresee J S, Glass R I, Ivanoff B, Gentsch J. Current status and future priorities for rotavirus vaccine development, evaluation and implementation in developing countries. Vaccine 1999; 17: 2207-22). In high-income countries, few children die from rotavirus whereas, globally, most children who die each year from rotavirus infection are from low-income countries. Studies of rotavirus vaccines in low-income countries have shown moderate efficacy, unlike high income countries inspite of the vaccination programs. A combination of factors, may be attributed to such moderate results of rotavirus vaccines in the developing countries which includes limited access to healthcare (hydration therapy), poor infrastructure, higher costs of transportations of vaccines, special features in the mode of administration of the vaccine, specificity of serotypic coverage, along with a greater prevalence of malnutrition. Present research in this area necessitates further study of rotavirus vaccines in low-income countries and identify new ways to improve vaccine performance. Most importantly, the stability of the rotavirus vaccine formulations requires to be enhanced to overcome costly and long-term transportation and storage facilities in these low-income countries of interest. Although, the prior patents available in the field of rotavirus vaccines against rotavirus infections provide with experimental data for stability of the rotavirus vaccine formulations, practical implications on the present status of the art reflect major stability hurdles after the first year from date of manufacture of the vaccine. Therefore, effective stability studies are required to be shown for rotavirus vaccine formulations for at least 24 months of storage in order to ensure worldwide vaccination programs across least developed or other low-income countries wherein the fight against rotavirus may be considered to be still in its initial stage.

Rotavirus is an acid-labile virus having a half-life of less than 12 minutes at pH 2.0. It is rapidly inactivated at such acidic pH. The rotavirus vaccines are intended to be administered to the infants by the oral route, wherein the antigen in the rotavirus vaccine is most likely to be inactivated by stomach gastric acid. Therefore, to prevent inactivation of the virus by gastric acid, antacids or buffers are needed to be administered before or in combination with the oral rotavirus vaccination.

With U.S. Pat. No. 6,616,931 Merck, the first to enter in the domain of rotavirus vaccines. U.S. Pat. No. 6,616,931 claimed a rotavirus vaccine composition comprising a Liquid rotavirus vaccine formulation comprising a strain of rotavirus: ($1 \times 10^5$ to $1000 \times 10^5$ pfu/ml), a sugar selected from the group consisting of: sucrose, lactose [1% to 70% w/v], mannitol, sorbitol, dextrose, fucose, trehalose, poly-aspartic acid, or N-acetylneuraminic acid, inositol-hexphosphate (phytic acid), and sialic acid, a phosphate [0.01M to 2M] selected from the group consisting of monophosphate, polyphosphate, phosphorylated sugars, and a carboxylate [0.05M to 2M] selected from the group consisting of succinate (0.05 M), citrate (0.07 M), fumarate, tartarate, maleate, lactate, recombinant Human Serum Albumin (0.5 to 1.25%), and polysorbate (0.1 to 2%) to liquid and lyophilized formulations. In case of lyophilized formulation nonionic surfactant selected from the group consisting of polysorbates, polysorbate80 (0.00 to 0.1%) is claimed. Citrate and Phosphates in the ranges of 0.05 M to 2 M and 0.01 M to 2 M have been used as buffering agents to counter the acidic environment of the stomach gastric acid in the rotavirus formulation. The commercialized vaccine "Rotateq" of Merck includes 5 live rotavirus strains (G1, G2, G3, G4, and P1), sucrose, sodium citrate, sodium phosphate monobasic monohydrate, sodium hydroxide, polysorbate 80 and fetal bovine serum. This commercially available rotavirus vaccine reflects the composition to its granted U.S. Pat. No. 6,616,931. The Rotateq vaccine had been made available in a 2 ml liquid solution for oral administration of 5 live human-bovine reassortant rotaviruses containing a minimum of $2.0$-$2.8 \times 10^6$ infectious units (IU) per reassortant dose, depending on the serotype, and not greater than $116 \times 10^6$ IU per aggregate dose.

However, U.S. Pat. No. 6,616,931 (WO2002/011540) also quotes that lyophillization of rotavirus vaccines can result in loss of viral titer during freeze-drying. This may result in low yields, and the potency of the lyophilized vaccine formulation as well is subject to be reduced below required levels resulting ineffective immunization. It also recognizes that prior reconstitution of a lyophilized formulation is subject to losing potency at room temperatures. Buffering agents for liquid formulations disclosed in this patent includes citrate, phosphate, succinate, bicarbonates and in combinations of other carboxylates such as fumarate, tartarate, lactate and maleate. Further, concentration of phosphate is taught to be kept lower than 0.35 M to avoid precipitation of the viral vaccine formulation. Use of bicarbonates for stabilizing the viral vaccine formulation is also expressly discouraged since it is taught to be detrimental to the stability of the formulation. Additionally, working examples of various buffer components except to those of citrates, succinates and phosphates are missing in the specification. Therefore, it seems that a need for novel buffer components exists for enhanced stability of the rotavirus vaccine and buffer liquid formulations.

Following Merck, Glaxo Smithkline also filed and subsequently granted U.S. Pat. No. 7,285,280 on rotavirus vaccine formulation. U.S. Pat. No. 7,285,280 claims a live attenuated rotavirus vaccine composition formulated with an organic antacid Sodium Citrate, or inorganic antacid Aluminium Hydroxide or Calcium Carbonate, and xanthane gum for oral administration. The vaccine formulation is lyophilized with Calcium Carbonate present as the antacid to be reconstituted with aqueous solution prior to administration. Alternatively, this patent also claims a vaccine formulation as a quick dissolving tablet in lyophilized form to be directly placed on the tongue of an infant/child wherein the rotavirus antigen, the antacid and xanthane gum are already present in the tablet. Accordingly, corresponding product prescription to U.S. Pat. No. 7,285,280 of commercially available "Rotarix", of GSK is a lyophilized vaccine which needs to be reconstituted before administration by adding the diluent provided separately with the vaccine. "Rotarix powder and solvent for oral suspension" contains live attenuated human rotavirus RIX4414 strain produced on Vero cells not less than $10^{6.0}$ CCID$_{50}$, sucrose 9 mg and sorbitol 13.5 mg, dextran, Dulbecco's Modified Eagle Medium (DMEM), amino acids in the lyophilized powder whereas the reconstitution solvent includes, xanthan gum, calcium carbonate and sterile water. The vaccine dose after reconstitution is 1 ml and two separate doses are needed to be administered with a time interval of at least 4 weeks between the first and the second dose. Although a dosage formulation of 1 ml has been made available, it is not made available as an entirely stable single liquid formulation in practical terms. The vaccine formulation of Rotarix is lyophilized one, and comes with a separate oral applicator containing the diluent and a glass vial containing the lyophilized vaccine antigen in powder form along with a separate transfer adapter. A detailed 10 separate steps have to be chronologically followed in proper order to ensure proper reconstitution. This reconstitution of the vaccine by mixing vaccine and diluent has its own disadvantages. Administration of this vaccine undergoes a tedious process of first connecting the transfer adapter to the glass vial containing the vaccine antigen in powder form, followed by connecting the transfer adapter to the oral applicator, mixing the vaccine antigen and the diluent properly, ensuring the turbidity of the reconstituted solution, removing the transfer adapter, and then administering the vaccine. All these steps separately require efficient operative skills of the person/health care provider who is administering the vaccine to the infant/child/patient. Therefore it is still desired to have a single liquid formulation with appropriate dose volumes of rotavirus vaccine formulations.

Subsequently GSK's U.S. Pat. No. 8,192,747 claims a liquid oral rotavirus formulation comprising live attenuated rota virus antigen, a sugar (35% to 70% w/w) selected from sucrose, mannitol, maltose, dextrose, lactose and trehalose (40%-70%), a carboxylate which is sodium adipate (50 mM to 2 M restricted to 100 mM to 1 M further restricted to 400 to 700 mM and a carboxylic acid, Adipic Acid along with calcium ions, wherein the composition has an antacid capacity of at least 12 minutes. The carboxylates proved to have buffering capacity in this patent includes among others citrates, acetates, malonates, malates, glutamates, fumarates, lactobionates, maleates, glucouronates, galactouronates, galactarates, and tartarates along with corresponding acid and sodium hydroxide salt. Additionally, formulations disclosed in this patent also may include certain commercially available antacid components as well, preferably aluminium hydroxide and magnesium hydroxide, other water insoluble antacids mentioned are magnesium carbonate, aluminium carbonate, aluminium phosphate, mix of aluminium hydroxide and magnesium carbonate, aluminium magnesium hydrocarbonate, aluminium hydroxide-magnesium carbonate-sorbitol-mannitol, hydroxy-aluminium-sodium-carbonate, dihydroxy aluminium potassium carbonate. Although a list of antacids have been referred in this patent, stability of a vaccine formulation with a particular antacid has to be established. Further, antacid action on the live virus, while present as an ingredient to the vaccine formulation with other vaccine antigen and other stabilizers/preservatives or excipients is also questionable. Commercially available antacids mixed with vaccine formulations might cause the vaccine antigen to coagulate and form thick masses of the liquid formulation. Moreover, in liquid vaccine formulations, antacid remains much as a suspension and therefore not advisable to be included in the vaccine formulation. The product specification of commercially available next generation Rotarix vaccine of GSK provides a liquid vaccine formulation, "Rotarix oral suspension in pre-filled oral applicator" containing live attenuated Human rotavirus RIX4414 strain not less than $10^{6.0}$ $CCID_{50}$, produced in Vero cells, sucrose 1073 mg, Di-sodium Adipate, Dulbecco's Modified Eagle Medium (DMEM) and sterile water in a 1.5 ml dosage form to be administered orally.

Bharat Biotech International Limited owns a granted patent 242868 in India (PCT publication WO2007/132480) which also discloses unique rotavirus vaccine formulation which is stable at 2°-8° C. using citrate-phosphate buffers in the ranges of 100 mM to 150 mM and 310 mM to 400 mM respectively along with its other distinct formulation components. This patent involves separate administration of Citrate-Bicarbonate to the subject prior to the administration of the vaccine. According to this patent, Citrate-Bicarbonates are not included in the formulation itself. The present invention overcomes this drawback wherein the use of Citrate-Bicarbonate buffer system present in the vaccine formulation together with the rotavirus antigen, has been proved to retain the buffering capacity without affecting the vaccine stability of the formulation. Bharat Biotech's PCT publication WO2011/07363 has subsequently claimed and disclosed a novel bioprocess for preconditioning with Human Serum Albumin during virus-infected host cell propagation, thereby giving better characteristics of the vaccine stability.

As it is mentioned above, in rotavirus vaccine formulations, a particular buffer component is necessary to combat the gastric acid environment of the stomach. Although the initial GSK's commercial rotavirus vaccine formulations included antacids, but the latest commercial version of rotavirus vaccine of GSK has switched from antacids to buffers. In a simplistic manner, it could be stated that, an antacid is known to neutralize the pH of the stomach acidic environment, whereas a buffer retains the pH of the vaccine formulation itself in the highly acidic environment of the stomach. It is always advantageous to mix buffers into a formulation which can protect the vaccine antigen from gastric acid of the stomach, and also maintain vaccine stability as well.

A list of either buffering components, or antacids have been cited in the prior art for countering the gastric acid environment, the most preferred being citrate phosphate buffers. The current state of the art recognizes some inherent problems of using citrate phosphate buffers in vaccine formulations. They are the most physiological of the common buffers and mimic certain components of extracellular fluids, still they have a number of potential disadvantages. For instance, phosphates inhibit many enzymatic reactions including cleavage of DNA by restriction enzymes, ligation of DNA and bacterial transformation. Phosphates are more likely to become easily contaminated with micro-organisms and tend to precipitate during fixation. The US'931 patent family of Merck discourages use of Phosphates as a buffer above a certain limit of 0.35 M to avoid precipitation of phosphate salts in the vaccine formulations. The GSK's US'797 patent expressly mentions that the rotavirus vaccine formulations are preferably free of phosphates. Sodium Citrate has been used by GSK in its US'280 patent as an inorganic antacid. However, use of citrates by GSK in its subsequent US'797 as a buffer seems completely withdrawn. The US'797 claims carboxylates which is expressly intended to be derived from a di-carboxylic acid. Citrate Buffers are derived from citric acid. Citric acid has three carboxyl functional groups. Citrate buffers are prepared by mixing citric acid and preferably sodium citrate to get the desired pH. Therefore, citrate buffers are buffers prepared from tricarboxylic acids.

It is also evident from the background disclosure that, rotavirus vaccines require either antacids or buffers to withstand the highly acidic environment in the stomach. Buffers are important because, the suspended rotavirus antigen in a solution must not experience a loss of potency and should interact in a favourable manner with the rest of the excipients to optimise vaccine efficacy. They are crucial to the efficacy and stability of vaccines as dramatic increases or decreases in the pH of the solution can cause denaturation of the protein/rotavirus live antigen in the vaccine. The buffer to be used with the vaccine formulation requires the fulfilment of the criteria of being inexpensive and easy to prepare as well as resistant to oxidation to be stable. It is also important to choose a buffer that is not toxic to the preparation. A suitable buffer system should not reduce the titer of the antigen vaccine, as well as function as a potential ingredient to combat the highly acidic environment inside the patient to which the vaccine ought to be administered. Buffers being integral part in rotavirus vaccines, since they required to retain the pH of the vaccine formulation in the highly acidic pH of the stomach also needed to be ensured that the vaccine titer is not vitiated below its immunogenic levels. Buffers being another ingredient of rotavirus vaccine formulations intended to counter the acidic environment of stomach require establishing the stability of the vaccine formulation for its long-term use. Possibilities of use of other carboxylates as buffers might have been referred in the prior art, yet absolute and specific combinations of these buffers with antigen and other stabilizing excipients of the rota virus vaccine formulation is required to be established. Specific combination of appropriate buffers with antigen in one single vial, should not show any formation of precipitates, and must show long term stability. Despite an exhaustive list of many possible buffer components finds a mention in the prior arts of Merck and GSK, a biological composition cannot be accepted with mere assumptions and possibilities wherein the state of the art has not been supported by any experimental data. Merely Citrates, Phosphates, and to some extent Succinates have been experimentally shown in the prior art as the most widely acceptable buffers in vaccines.

Buffers are known to act in combination systems. Each combination buffer systems are specific to have its own unique physico-chemical properties and buffering capacity. Selection of a particular buffering combination system in a particular solution depends upon the kind of the composition. The present invention deals with rotavirus vaccine compositions which include live attenuated virus and a wide range of other formulation components such as one or more sugars, and partially hydrolysed proteins along with in presence of other possible stabilizing components. The components interact in a wide variety of ways with each other, and therefore, selection of a particular buffer-combination system that fits into the kind of a particular formulation thereby retaining its functional activity must be acknowledged. Contrary to possible buffers merely cited in the prior art, novel combination buffer systems which have not been cited in the prior art and their role in stabilizing the rotavirus vaccine formulations have been presented in details in the present invention, key feature being minimum of 2 years stability.

Therefore, novel vaccine compositions with novel buffers combination systems are invented for rotavirus vaccine formulations which are additionally safe and effective as well to ensure maximum rotavirus vaccine efficacy at the same time is also stable for comparatively higher amounts of time to effectuate better transportation of the rotavirus vaccines across the globe. The present invention proposes the use of novel buffer combination systems which are all absent in the prior art for rotavirus vaccine preparations capable of being readily ingested and assimilated by the human body without compromising on the viral titer and at the same time highly stable as well. Overcoming the existing limitations associated with rotavirus vaccine formulations with such ideal vaccine and buffer formulation(s) as described herein this invention will be of great advantage in worldwide vaccination against rotavirus infections.

Lyophilized vaccine formulations have extended stability but incur higher manufacturing costs. The logistics involved in case of lyophilized vaccines also decreases the chances of making rotavirus vaccines available in remote areas of the world. Sophisticated transportation facility for lyophilized vials adds on to the issue of logistics and increased expenditure of the vaccines. Therefore, inventors of the present invention have experimentally shown liquid rotavirus vaccine formulations with novel alternate buffers in a range of dose volumes including as low as 1 ml formulations to 2.5 ml dose volume formulations. for an extended period of up to at least 2 years. This is a considerable advancement over the current state of the art available on rotavirus vaccine formulations. Stable rotavirus vaccine formulations up to 2 years at refrigeration temperatures will facilitate easy transportation of the vaccines at much lower costs at the same time, maintaining the viral titer in the formulation to raise the required immunogenecity will also be made possible at ease.

OBJECTS OF THE INVENTION

Primary object of the invention is development of a vaccine formulation for prophylaxis and treatment of rotavirus infections in humans.

Another object of the invention is to provide rotavirus vaccine composition with suitable alternate novel buffers for providing stability to the rotavirus antigen in the vaccine composition.

Yet another object of the invention is to provide a rotavirus vaccine composition with novel alternate buffers which would retain the pH of the rotavirus vaccine composition at high acidic stomach pH during administration of the vaccine.

Another object of the invention is to provide a stable rotavirus vaccine composition with stabilizers and buffers for oral administration without requiring pre-administration of an antacid.

A further object of the invention is to provide a stable rotavirus vaccine composition that would enable long term stability of the rotavirus antigen without losing the potency of the vaccine as long as up to at least 2 years.

Yet, another object of the invention is to provide a method of adaptation of rotavirus in presence of recombinant trypsin for preparation of a novel rotavirus vaccine composition which is devoid of any contamination from animal sources as well as absolutely free from other animal origin.

BRIEF DESCRIPTION OF THE DRAWINGS

FIG. 1: Baby Rossete Rice Assay results of various formulations to study the buffering capacity of the formulations.

FIG. 2: Stability of rotavirus vaccine formulations at 2-8° C. with citrate phosphate buffers.

FIG. 3: Stability of rotavirus vaccine formulations at 25° C. with citrate phosphate buffers.

FIG. 4: Stability of rotavirus vaccine formulations at 37° C. with citrate phosphate buffers.

FIG. 5: Stability Studies of rotavirus vaccine formulations using Citrate Bicarbonate Buffers at 2°-8° C.

FIG. 6 Stability Studies of rotavirus vaccine formulations using Citrate Bicarbonate Buffers at 25° C.

FIG. 7: Stability Studies of rotavirus vaccine formulations using Carbonate Bicarbonate Buffers at 2-8° C.

FIG. 8: Stability Studies of rotavirus vaccine formulations using Carbonate Bicarbonate Buffers at 25° C.

FIG. 9: Stability Studies of rotavirus vaccine formulations using Magnesium Hydroxide Carbonate Buffers at 2-8° C. and 25° C.

FIG. 10: Stability Studies of rotavirus vaccine formulations using Mixed Buffers at 2-8° C.

FIG. 11. Stability of rotavirus vaccine formulations at 25° C. with ammonium based Mixed Buffers.

FIG. 12. Stability of rotavirus vaccine formulations at 37° C. with ammonium based mixed buffers.

FIG. 13: Effect of Different Buffers on ORV formulations on log titer vs. time.

FIG. 14: Effect of Different Buffers on ORV formulations on log loss titer vs. time.

DESCRIPTION OF THE INVENTION

Definitions:

FFU/ml: A measurement of the concentration of the live virus in a given amount of fluid/harvest. This is measured by spreading a known amount of the viral fluid over a layer of cultured cells which are infected by the virus, then counting the number of areas in the culture which look infected.

Target titer: Each single human dose of rotavirus vaccine should contain not less than $10^{5.5}$ ffu/dose to raise the vaccine immunogenecity, till end of shelf life of the vaccine which is referred as the Target Titer.

The required virus bulk is added on the basis of bulk titer and the target titer for the formulation on volume basis. Typical rota virus bulk titers are around $10^{7.5}$ per dose while the formulation titers were targeted around $10^{6.0}$ or $10^{5.5}$ per dose, except a few batches were also formulated around $10^{4.0}$ titer to check the effect of vaccine titer on stability for a given composition. All components are finally expressed in weight/volume percentage terms.

Typical target titer was around $10^{6.0}$ at the time of preparation of the vaccine; the objective being to achieve a vaccine formulation with a titer at the minimum of $10^{5.0}$ after giving an allowance of 0.5 log loss in titer (with a margin for titer estimation error around +/−0.30), after 2 years of storage at 2°-8° C. Any composition which shows a titer loss greater than 0.3 compared to the zero day titer at 2-8° C. is considered as exhibiting signs of instability. Of course, titer losses are quite high at 25° C. and 37° C. as a function of storage time, but these results are used only for screening purposes.

The total dose volume exemplified in the various formulations ranges from 0.5 ml to 2.0 ml has formulations considering the fact that, the vaccine is able to be easily absorbed by the infant. The excipients (sugars) are dissolved in the desired novel buffer solution(s) as is a common practice in biological preparations while the stabilizers [(Human Serum Albumin (HSA)/Lactalbumin Hydrolysate (LAH)] are made as aqueous solutions (in Water For Injection) and all solutions are sterile filtered. Both these solutions are prepared on weight/volume basis. While vaccine+ buffer is known with 2.5 ml as the total volume, based on acid neutralization studies, lower buffer volumes have also been tested. This was also corroborated with information available in public domain on commercial rotavirus vaccines.

As required, detailed embodiments of the present invention are disclosed herein with the help of examples; however, it is to be understood that the disclosed embodiments are merely examples of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting but rather to provide an understandable description of the invention.

Example 1: Method of Adaptation of Rotavirus in Presence of Recombinant Trypsin Small scale studies were conducted using T flasks and CF1 (Cell Factory 1), further scaled upto CF40 to study the comparative infectivity and yields of Rotavirus in Vero cells. Post infection, fluid viral harvest (VH) per ml in terms of yield of harvest was observed after every 48 hours. Three sets of experiments were conducted using T Flasks and Cell Stacks and average of the three experiments was considered and the results are shown in the table below.

TABLE 1

Yield of viral harvest taken after every 48 hours post infection in presence of recombinant trypsin and trypsin (animal origin).

| Type of Trypsin used | Container used | VH I (48 hrs) | VH II (96 hrs) | VH III (144 hrs) |
|---|---|---|---|---|
| Porcine Trypsin | T 175 Flask | 6.52 | 6.97 | 6.75 |
| Recombinant Trypsin | T 175 Flask | 6.85 | 7.08 | 6.92 |
| Porcine Trypsin | CF 1 | 6.88 | 7.05 | 7.12 |
| Recombinant Trypsin | CF 1 | 7.03 | 7.48 | 7.21 |
| Porcine Trypsin | CF 40 | 6.83 | 7.23 | 6.76 |
| Recombinant Trypsin | CF 40 | 6.95 | 7.38 | 6.87 |

Hence, it is evident from the experiments that Recombinant Trypsin has given comparatively better yields than Porcine Trypsin since Porcine Trypsin contains Chymotrypsin as impurity as well as free of any potential hazards associated with PCV 1 and 2, along with PCBs as well.

Example 2: Buffering Capacity of Various Novel Buffers and Vaccine with Buffer Formulations An ideal buffer can be selected by measuring the buffering capacity of a particular buffer. Buffering capacity is measured as the amount of buffer which would maintain pH to neutral conditions of a given formulation, in highly acidic environments. Usually the closer the buffered pH is to the pKa, the greater is the buffering capacity. The buffering capacity of various buffers was tested using 34 mEq of Hydrochloric acid. The buffering capacity results acted as a base to include such buffers in vaccine formulations. The buffering capacity of buffers and vaccine formulations were conducted using 34 mEq of Hydrochloric Acid and the well established Baby Rosette Rice Assay undertaken in the prior art.

Example 2.1: Buffering Capacity of Various Buffers

Following novel buffers have been checked for their buffering capacities which might be included in the rotavirus vaccine formulations:

TABLE 2 (a)

Buffering capacity of other buffer(s) that may be used as potential vaccine + buffer formulations with viral vaccines.

| Buffer details | 34.8 mEq HCl was used to simulate gastric juice. | | | | | | |
|---|---|---|---|---|---|---|---|
| 0.1M Trisodium Citrate | Volume of HCl | 0 ml | 5 ml | 10 ml | 15 ml | 20 ml | 25 ml |
| and 0.3M Potassium Phosphate | Volume of buffer | — | 1 ml | 1 ml | 1 ml | 1 ml | 1 ml |
| Buffer Combination system | pH | 7.57 | 6.89 | 6.21 | 5.75 | 5.11 | 4.68 |
| 0.3M Magnesium Hydroxide | Volume of HCl | 0 ml | 5 ml | 10 ml | 15 ml | 20 ml | 25 ml |
| Carbonate Buffer System | Volume of buffer | — | 1 ml | 1 ml | 1 ml | 1 ml | 1 ml |
| | pH | 10.5 | 8.02 | 7.82 | 7.68 | 7.48 | 6.55 |
| 0.2M Sodium Lactate + | Volume of HCl | 0 ml | 5 ml | 10 ml | 15 ml | 20 ml | 25 ml |
| 0.1M Sodium Bicarbonate | Volume of buffer | — | 1 ml | 1 ml | 1 ml | 1 ml | 1 ml |
| Buffer Combination System | pH | 8.02 | 7.48 | 6.92 | 6.22 | 5.83 | 5.01 |

TABLE 2 (a)-continued Buffering capacity of other buffer(s) that may be used as potential vaccine + buffer formulations with viral vaccines.

| Buffer details | 34.8 mEq HCl was used to simulate gastric juice. | | | | | | |
|---|---|---|---|---|---|---|---|
| C 0.2M Sodium Carbonate | Volume of HCl | 0 ml | 5 ml | 10 ml | 15 ml | 20 ml | 25 ml |
| and 0.2M Sodium Bicarbonate | Volume of buffer | — | 1 ml | 1 ml | 1 ml | 1 ml | 1 ml |
| Buffer Combination System | pH | 9.6 | 9.03 | 8.6 | 8.21 | 7.84 | 7.22 |
| 60% Sodium lactate solution | Volume of HCl | 0 ml | 5 ml | 5 ml | | | |
| | Volume of buffer | — | 1 ml | 2 ml | | | |
| | pH | | 4.08 | 6.02 | | | |
| C 0.03M Trisodium Citrate | Volume of HCl | 0 ml | 5 ml | 10 ml | 15 ml | 20 ml | 25 ml |
| and 0.3M Sodium Bicarbonate | Volume of buffer | — | 1 ml | 1 ml | 1 ml | 1 ml | 1 ml |
| Buffer Combination system | pH | 8.53 | 8.45 | 7.51 | 7.03 | 6.58 | 6.02 |

Conclusions:

Magnesium Hydroxide Carbonate, Carbonate-Bicarbonate Buffer and Citrate-Bicarbonate Buffer Combination Systems are strong buffers and even after addition of 20 ml concentrated Hydrochloric acid (HCl) also, pH came down to around 6.5 to 7.0 from the original pH. Lactate Bicarbonate buffer and 0.05M citrate and 0.1M Bicarbonate Buffers are moderate wherein the pH reaches to 5.5 to 6.0 after addition of 20 ml of HCl. All the above said buffer(s) are able to neutralize 5 ml of HCl where the pH is in the range of 9.0 to around 7.0. since the volume of gastric juice is approximately 3.0 ml to 5.0 ml, all these buffers can be used as buffers for retaining the vaccine pH in the stomach. When these buffers are used for formulation, due to the presence of other excipients along with buffers 1 ml of vaccine is able to neutralize 5 ml of acid, but pH is around 6.0 instead of 7.0. pH 6.0 will not destabilize the viral antigen and hence these buffers can be added to oral vaccine formulations.

Apart from the above mentioned novel buffers ammonium acetate based mixed buffers were checked for buffering capacity Ammonium acetate based mixed buffer combination systems have not been cited in any prior art literature relating to rotavirus vaccine formulations. The buffering capacity of such ammonium based mixed buffers have been evaluated. Mixed Buffers with Ammonium Salts (Ammonium acetate+Ammonium bicarbonate+Di ammonium ortho phosphate of 0.5 M) was checked to confirm its buffering capacity. To 0.5 ml of concentrated Hydrochloric Acid, Mixed Buffer was added from 0.5 ml to 2 ml and pH was checked.

TABLE 2(c)

Buffering capacity of mixed buffer with ammonium salts

| | pH Results (0.5 ml Acid + Buffer) | | | |
|---|---|---|---|---|
| Buffer volume added to 0.5 ml of concentrated Hydrochloric Acid. | 0.5 ml | 1.0 ml | 1.5 ml | 2 ml |
| pH of Mixed Buffer (0.5M) | 7.25 | 7.74 | 7.90 | 7.98 |

It is evident from the above table that even after addition of Concentrated Hydrochloric Acid to 0.5 ml of buffer, the buffer is able to retain the pH of 7.25 which indicates that these Ammonium buffers are strong buffers which can resist the pH changes upon the addition of Concentrated Acid and also when the buffer is added progressively from 0.5 ml to 2.0 ml pH, increased in the range of 7.7 to 8.0.

Example 2.2: Buffering Capacity of Various Vaccine and Novel Buffer Formulations In our efforts to develop stable novel vaccine and buffer compositions, a large number of formulations have been prepared with various buffers at a wide range of concentration. A few guiding factors have been framed while developing such compositions:
  Acid Neutralizing Capacity or Buffering Capacity of the chosen buffer.
  Volume of buffer required to be less than 2.0 ml for the prescribed acid system.
  Stability of the buffer+virus vaccine combination.

For such studies, the pure liquid vaccine compositions without buffers which have been found to be stable at 2°-8° C. have served as the base compositions. Again to recapitulate, compositions which show a titer loss less than 0.5 log or those whose final titer is greater than 105.50 are considered to be stable compositions.

2.2.1.

Buffering capacity using 34 mEq HCl of various vaccine formulations with Citrate Bicarbonate, Carbonate Bicarbonate and Citrate Phosphate Buffer was also tested and provided in the table mentioned below.

TABLE 2(b)

Buffering capacity of various rotavirus formulations with buffers.

| Formulation | | Buffering Capacity | |
|---|---|---|---|
| Example No. | Composition Details | Volume Added | pH |
| BV-1 | Rotavirus antigen 116E | 0.5 ml | 2.97 |
| | Sucrose 40% | 1.5 ml | 5.01 |
| | Trehalose 0.5% | 1.7 ml | 5.73 |
| | Lactose 5.0% | | |
| | Lactalbumin Hydrolyzate 0.5% | | |
| | Recombinant Human Serum Albumin 0.35% | | |
| | 0.03M Trisodium Citrate + 0.3M Sodium Bicarbonate Buffer | | |

TABLE 2(b)-continued

Buffering capacity of various rotavirus formulations with buffers.

| Formulation Example No. | Composition Details | Buffering Capacity Volume Added | pH |
|---|---|---|---|
| BV-2 | Rotavirus antigen 116E<br>Sucrose 40%<br>Trehalose 0.5%<br>Lactose 5.0%<br>Recombinant Human Serum Albumin 0.35%<br>Lactlabumin Hydrolysate 0.5%<br>0.1M Trisdoium Citrate + 0.3M Potassium phosphate Buffer | 0.5 ml<br>0.8 ml | 5.93<br>6.25 |
| BV-3 | Rotavirus antigen 116E<br>Sucrose 40%<br>Trehalose 0.5%<br>Recombinant Human Serum Albumin 0.35%<br>Lactalbumin Hydrolysate 0.5%<br>0.1M Sodium Carbonate - Sodium Bicarbonate Buffer | 0.5 ml<br>1.0 ml<br>1.3 ml | 2.94<br>3.78<br>5.76 |
| BV-4 | Rotavirus antigen 116E<br>Sucrose 40.0%<br>Trehalose 0.5%<br>Lactose 0.5%<br>Recombinant Human Serum Albumin 0.35%<br>Lactalbumin Hydrolysate 1.0%<br>ZnCl$_2$ 3 mM<br>0.1M Sodium Carbonate - Sodium Bicarbonate Buffer | 0.5 ml<br>1.0 ml<br>1.5 ml | 2.72<br>3.40<br>5.63 |
| BV-5 | Rotavirus antigen 116E<br>Recombinant Human Serum Albumin 1.60%<br>Lactalbumin Hydrolysate 1.0%<br>0.1M Sodium Carbonate - Sodium Bicarbonate Buffer | 0.5 ml<br>0.8 ml<br>1.0 ml | 3.49<br>5.76<br>6.62 |
| BV-6 | Rotavirus antigen 116E<br>Sucrose - 40%<br>Trehalose - 0.5%<br>Lactose - 5.0%<br>Recombinant Human Serum Albumin - 0.35%<br>Lactalbumin Hydrolysate - 0.5%<br>ZnCl2 - 3 mM<br>0.5M Ammonium based mixed Buffer | 0.5 ml<br>1.0 ml<br>1.5 ml | 3.71<br>4.65<br>6.05 |
| BV-7 | Rotavirus antigen 116E<br>Sucrose - 50%<br>Trehalose - 0.5%<br>Recombinant Human Serum Albumin - 0.35%<br>Lactalbumin Hydrolysate - 1.0%<br>0.1M Magnesium Hydroxide Carbonate Buffer | 0.5 ml<br>0.8 ml<br>1.0 ml | 3.41<br>4.5<br>5.94 |

2.2.2.

Baby Rossette Rice Assay: Since Rotavirus vaccine is administered orally, it will get exposed to gastric acidity where the pH is around 1.8 to 2.0 due to which rotavirus antigen will get inactivated. To prevent this inactivation of virus potential, buffers used in formulations retains the formulation at neutral pH levels. Rotavirus inactivation takes place at pH 2.0 or 3.0 but at pH 4.0, no or minimal inactivation takes place. The buffering capacity of a given formulation is defined as the time measured to maintain the pH of the formulation above 4.0 and is evaluated by Baby Rossette Rice assay which is a validated method and referred in the prior art.

Procedure for BRR Assay: In a 50 ml beaker Water For Injection was added to the formulation to a final volume of 10 ml. The beaker was placed in water bath and the temperature maintained at 37° C. The initial pH of the solution was measured and recorded. Thereafter, 4.0 ml of 0.1N Hydrochloric Acid was added to the beaker containing the final volume of 10 ml formulation. At the same time the pump for addition of 0.5 ml/minute of 0.1N HCl using peristaltic pump was switched on. The pH values along the time was recorded per minute, until the pH of 4.0 or above is retained. Stop the clock and pump. (Reference: Geigy scientific Tables, Volume 1, 1981 addition, Page 126). Several rotavirus vaccine formulations with novel buffer-combination systems were checked for buffering capacity (the respective components of the formulation details have been mentioned wherever applicable). Buffering capacity results are mentioned in the table below.

TABLE 2(d)

BRR assay results of novel buffer formulations and reference formulations (FIG. 1)

| | Time (minutes) | | | | | | | | | | | | | | | | | | |
|---|---|---|---|---|---|---|---|---|---|---|---|---|---|---|---|---|---|---|---|
| | 0 | 1 | 2 | 3 | 4 | 5 | 6 | 7 | 8 | 9 | 10 | 11 | 12 | 13 | 14 | 15 | 16 | 17 | 18 |
| pH of CB Buffer | 8.58 | 6.52 | 6.67 | 6.90 | 6.86 | 6.75 | 6.63 | 6.38 | 6.15 | 5.80 | 5.11 | 4.37 | 3.69 | | | | | | |
| pH of BV-8 | 7.78 | 7.88 | 6.18 | 6.02 | 5.79 | 5.51 | 5.24 | 5.01 | 4.78 | 4.57 | 4.33 | 4.07 | 3.75 | | | | | | |
| pH of BV-9 | 7.93 | 6.50 | 6.40 | 6.31 | 6.19 | 6.07 | 5.93 | 5.70 | 5.44 | 5.20 | 4.96 | 4.74 | 4.55 | 4.37 | 4.15 | 3.91 | | | |
| pH of CPB | 6.75 | 5.40 | 5.30 | 5.18 | 5.06 | 4.95 | 4.83 | 4.69 | 4.58 | 4.47 | 4.36 | 4.23 | 4.09 | 3.98 | | | | | |
| pH of BV-10 | 7.03 | 5.53 | 5.32 | 5.10 | 4.62 | 4.76 | 4.6 | 4.43 | 4.29 | 4.12 | 3.97 | | | | | | | | |
| pH of BV-11 | 6.64 | 5.19 | 5.05 | 4.90 | 4.78 | 4.63 | 4.46 | 4.34 | 4.26 | 4.06 | 3.92 | | | | | | | | |

Citrate Bicarbonate buffer is 0.03 M Trisodium Citrate and 0.3 M Sodium Bicarbonate Buffer.

Formulation Example BV-8 contains sucrose 40.0% w/v, Trehalose 0.5% w/v, Lactose 5.0% w/v, Lactalbumin Hydrolysate 0.5% w/v, rHSA 0.08% w/v, 0.5 M Di Ammonium hydrogen ortho-phosphate, Ammonium acetate and Ammonium bicarbonate mixed buffer along with rotavirus antigen 116E of a dose volume of 1 ml.

Formulation Example BV-9 contains sucrose 30.0% w/v, Trehalose 2% w/v, Lactose 5.0% w/v, Lactalbumin Hydrolysate 1% w/v, rHSA 0.08% w/v, 0.5 M Di Ammonium hydrogen ortho-phosphate, Ammonium acetate and Ammonium bicarbonate mixed buffer along with rotavirus antigen 116E of a dose volume of 1.5 ml.

CPB is 0.35 M Trisodium Citrate and 0.05 M Potassium Phosphate Buffer.

Formulation Example BV-10 contains sucrose 40% w/v, trehalose-0.5% w/v, Lactalbumin Hydrolysate-0.5% w/v, rHSA-0.35% w/v, 0.05M Potassium Phosphate and 0.35M Trisodium Citrate buffer along with rotavirus antigen 116E, up to a dose volume of 2.0 ml.

Formulation Example BV-11 contains sucrose-40% w/v, trehalose-0.5% w/v, Lactalbumin Hydrolysate 0.5% w/v, rHSA-0.35% w/v, 1.1M Potassium Phosphate buffer upto a dose volume of 2 ml.

Conclusions:

2.5 ml of Citrate Bicarbonate has been also measured separately which were administered to infants separately prior to administration of the vaccine according to earlier practices which maintained pH of 4 and above for about 12 minutes. Formulation examples BV-8 and BV-9 of BBIL are the ammonium based mixed buffer batches and are able to neutralize and maintained the pH above 4.0 for about 15 minutes.

Certain formulation examples BV-10 include buffer combination system prepared wherein the citrate concentration is raised to 0.35 M and Phosphate is reduced to 0.05 M and checked for buffering capacity using 2.0 ml as dose volume. Buffering capacity was observed and found to be 12 minutes. This formulation also is able to neutralize enough acid and shows good buffering capacity. Hence in this buffer 0.35M Citrate was considered.

Example 3: Stability of Rotavirus Vaccine Formulations with Novel Buffers

Among the novel buffers, some of the most advantageous buffers showing better stability compared to others include the Carbonate-Bicarbonate buffer system, Magnesium Hydroxide Carbonate buffer, Citrate-Bicarbonate buffer system, and a mixed buffer with ammonium salts. The final stability of vaccines with these novel buffers along with final rotavirus vaccine formulations and processes of manufacturing the same have been performed.

The experiments include incorporation of Zinc ions for further stability of the final rotavirus vaccine formulations Zinc ions have been observed to enhance the stability of vaccine by interacting with the composition in a manner that is known in the art. Inge Erk et. al Journal of Virology, Vol. 77, No. 6 Mar. 2003, p. 3595-3601 demonstrates that, the major capsid proteins of the VP6 trimers of rotavirus play a significant role in achieving viral flexibility in presence of Zinc ions at a given pH and temperature. The novel formulations of rotavirus vaccine therefore, include Zinc ions also to render better stability to the rotavirus antigen in the final formulations.

The human Rotavirus strain 116E is a naturally attenuated (human-bovine reassortant). Stability studies of the final formulations with the rota virus antigen have been performed at various temperature ranges. Various vaccine formulations have been subjected to temperatures at 2° to 8° C., and 25° C. Observations of the vaccine titer were taken in terms of FFU/dose (focus forming units) which were taken at regular time intervals based upon the protocols. A maximum drop within the range of 0.3 log loss of the vaccine titer was considered to be maintained as a stable rotavirus vaccine formulation with the new buffer systems at 2-8° C. As explained earlier, virus titer of the vaccine is measured as a function of storage time to assess the formulation stability. For each cases, as described in the below examples, it was observed that, after 24 months of storage, at 2-8° C. the vaccine formulation was found to be stable (with a minimum or no loss considering the error bar). However, at room temperature a maximum of 1.5 log loss in vaccine titer was observed for a period of six months. Such a loss in vaccine titer concludes vaccine stability at 25° C. for six months.

Example 3.1: Stability of Rotavirus Formulations with Citrate-Phosphate Buffer Combinations Formulation Example BV-10 contains sucrose 40% w/v, trehalose-0.5% w/v, Lactalbumin Hydrolysate-0.5% w/v, rHSA-0.35% w/v, 0.05M Potassium Phosphate and 0.35M Trisodium Citrate buffer along with rotavirus antigen 116E, upto a dose volume of 2.0 ml. Formulation Example BV-11 contains sucrose-40% w/v, trehalose-0.5% w/v, Lactalbumin Hydrolysate 0.5% w/v, rHSA-0.35% w/v, 1.1M Potassium Phosphate buffer upto a dose volume of 2 ml.

Stability Data of BV-10 and BV-11 are Provided Below:

TABLE 3(a)

Stability at 2-8° C. of BV-10 and BV-11 (FIG. 2).

| Formulation Example No. | 0 Day | 1 M | 3 M | 6 M | 9 M | 12 M |
| --- | --- | --- | --- | --- | --- | --- |
| BV-10 | 6.00 | 6.03 | 5.98 | 6.01 | 5.93 | 5.98 |
| BV-11 | 6.38 | 6.21 | 6.25 | 6.11 | 6.31 | 6.28 |

TABLE 3(b)

Stablity at 25° C. of BV-10 and BV-11 (FIG. 3).

| B. No | 0 Day | 2 wk | 4 wk | 8 wk | 12 wk | 16 wk | 24 wk |
| --- | --- | --- | --- | --- | --- | --- | --- |
| BV-10 | 6.00 | 5.93 | 5.78 | 5.63 | 5.45 | 5.31 | 4.89 |
| BV-11 | 6.38 | 6.01 | 5.95 | 5.71 | 5.52 | 5.25 | 4.79 |

TABLE 3(c)

Stability at 37° C. of BV-10 and BV-11 (FIG. 4).

| B. No | 0 Day | 1 wk | 2 wk | 3 wk | 4 wk |
| --- | --- | --- | --- | --- | --- |
| BV-10 | 6.00 | 5.51 | 4.3 | 3.98 | 3.05 |
| BV-11 | 6.38 | 5.78 | 4.85 | 4.11 | 3.68 |

Example 3.2: Vaccine Formulations with 0.03M Citrate and 0.3M Bicarbonate Buffer (CB Buffer)

Trisodium citrate, dehydrate of (Molecular Weight 294.1 gm) to an amount of 9.6 gm and Sodium bicarbonate anhydrous (Molecular Weight. 84.01 gm) to an amount of 25.6 gm was sequentially added to 500 ml in a sterile glass bottle so as to achieve 0.032M of Citrate and 0.3M of Bicarbonate. The components were dissolved completely and the volume was made up to 1 liter with WFI (water for injection). pH was checked and maintained to a level between 8.2 and 8.4. The buffer vessel was then transferred into 2 L Stainless Steel (SS) pressure vessel and connected with filter. The solution was filtered through 0.2μ filter under Biosafety Cabinet by using compressed air. The buffer was collected into another sterile bottle and the bottle was labeled and stored at 2-8° C. for future use.

Formulations were made using this (0.032M) Citrate (0.3M) Bicarbonate buffer combination system prepared including Rotavirus antigen 116E at $10^6$ ffu/dose and other stabilizers and components as mentioned below at dose volumes as mentioned in the following table corresponding to each formulation (identified by unique formulation number as appropriate allotted by Bharat Biotech International Limited in the tables), and stability of the vaccine formulation at 2° to 8° C., and 25° C. was tested at various time intervals till 2 years approximately which is given in the accompanying graphs (FIGS. 5 and 6).

TABLE 3(d)

Rotavirus Vaccine Formulations with CB Buffers.

| Formulation No. | Dose Vol | Formulation details | Buffer used |
|---|---|---|---|
| BV-12 | 1.5 ml | Rota virus antigen 116E, Sucrose 71.00%, Trehalose 0.50%, HSA 0.35%, LAH 1.00% | 0.03M Citrate + 0.3M Bicarbonate Buffer |
| BV-13 | 1 ml | Sucrose 30.00%, Lactose - 5.00%, HSA 0.35%, LAH 0.50%, 3 mM Zn | 0.03M Citrate + 0.3M Bicarbonate Buffer |
| BV-14 | 1.5 ml | Sucrose 71.0%, Trehalose - 0.5%, LAH 0.5% | 0.03M Citrate + 0.3M Bicarbonate Buffer |

TABLE 3(e)

Rotavirus Vaccine Stability at 2-8° C. with CB Buffer (FIG. 1)

| Formulation No. | 0 Day | 1 M | 4 M | 6 M | 12 M | 18 M | 24 M |
|---|---|---|---|---|---|---|---|
| BV-12 | 6.31 | 6.12 | 6.08 | 6.04 | 6.18 | 5.98 | 6.01 |
| BV-13 | 6.27 | 6.03 | 6.14 | 6.07 | 5.97 | 6.03 | 5.93 |
| BV-14 | 6.35 | 6.19 | 6.21 | 6.18 | 6.21 | 6.12 | 6.07 |

TABLE 3(f)

Rotavirus Vaccine Stability at 25° C. with CB Buffer (FIG. 2)

| Formulation No. | 0 Day | 2 wk | 4 wk | 6 wk | 10 wk | 16 wk | 24 wk (6 M) |
|---|---|---|---|---|---|---|---|
| BV-12 | 6.31 | 6.24 | 5.83 | 5.89 | 5.76 | 5.74 | 4.94 |
| BV-13 | 6.27 | 6.11 | 5.72 | 5.83 | 5.61 | 5.55 | 4.72 |
| BV-14 | 6.35 | 6.20 | 6.01 | 5.93 | 5.52 | 5.43 | 4.89 |

Example 3.3: Vaccine Formulations with Carbonate and Bicarbonate Buffer(s) (0.2M and 0.1M) (CAB Buffer)

One of the other well suited buffer systems to use for vaccine preparations that will be ingested and assimilated by the human body, is the carbonate-bicarbonate buffer system. This is because this buffer system is responsible for about 80% of extracellular buffering and is present in blood plasma in the form of a combination of carbonic acid (H2CO3) and bicarbonate (HCO3-) to maintain a pH between 7.35-7.45. This system is highly conducive to use in an organic environment as it fulfils the requirements of non-inhibition of enzymatic action, useful alkaline pH range, simplicity and reasonable good stability. This combination buffer system, has not been reported in the prior art, especially at bicarbonate molarities less than 0.15M.

Example 5.1: 0.2 M Carbonate Bicarbonate Buffer

Sodium carbonate anhydrous (Molecular Weight 105.99 gm) to an amount of 1.69 gm and Sodium bicarbonate anhydrous (Molecular Weight. 84.01 gm) to an amount of 15.4 gm was sequentially added to 500 ml in a sterile glass bottle so as to achieve 0.2M of Carbonate and 0.2M of Bicarbonate. The components were dissolved completely and the volume was made up to 1 liter with WFI (water for injection). pH was checked and maintained to a level between 9.2 and 9.5. The buffer vessel was then transferred into 2 L Stainless Steel pressure vessel and connected with filter. The solution was filtered through 0.2μ filter under Biosafety Cabinet by using compressed air. The buffer was collected into another sterile bottle and the bottle was labeled and stored at 2-8° C. for future use.

Example 5.2: 0.1 M Carbonate Bicarbonate Buffer

Sodium carbonate anhydrous (MW. 105.99) to an amount of 0.53 gm and Sodium bicarbonate anhydrous (MW. 84.01) to an amount of 7.98 gm was sequentially added to 500 ml in a sterile glass bottle so as to achieve 0.1M of Carbonate and 0.1M of Bicarbonate. The components were dissolved completely and the volume was made up to 1 liter with WFI (water for injection). pH was checked and maintained to a level between 9.2 and 9.5. The buffer vessel was then transferred into 2 L Stainless Steel pressure vessel and connected with filter. The solution was filtered through 0.2 μl filter under Biosafety Cabinet by using compressed air. The buffer was collected into another sterile bottle and the bottle was labeled and stored at 2-8° C. for future use.

Formulations were made using this 0.2M Carbonate-Bicarbonate buffer combination system and 0.1M Carbonate-Bicarbonate buffer combination system prepared including Rotavirus antigen 116E at $10^6$ ffu/dose and other stabilizers and components as mentioned below at dose volumes as mentioned in the following table corresponding to each formulation (identified by unique formulation numbers as mentioned in Table 3(g)), and stability of the vaccine formulation at 2° to 8° C., and 25° C. was tested at various time intervals till 2 years approximately which is given in the accompanying graph (FIGS. 7 and 8).

TABLE 3(g)

Rotavirus Vaccine Formulations with CAB Buffers.

| Formulation No. | Dose Vol. | Formulation Details | Buffer used. |
|---|---|---|---|
| BV-15 | 1 ml | Sucrose 40%, Trehalose 0.5%, HSA 0.35%, LAH 1% | 0.2M Carbonate Bicarbonate Buffer |
| BV-16 | 1 ml | Sucrose 50%, Trehalose 0.5%, HSA 0.35%, LAH 1%, 3 mM Zn | 0.2M Carbonate Bicarbonate Buffer |
| BV-17 | 1 ml | Sucrose 50%, Trehalose 0.5%, HSA 0.35%, LAH 1% | 0.2M Carbonate Bicarbonate Buffer |
| BV-18 | 1.5 ml | Sucrose 71%, Trehalose 0.5%, HSA 0.35%, LAH 1%, | 0.1M Carbonate Bicarbonate Buffer |

TABLE 3(h)

Rotavirus Vaccine Formulation Stability at 2-8° C. with CAB Buffers (FIG. 3).

| B. No. | 0 Day | 1 M | 2 M | 3 M | 4 M | 6 M | 9 M | 12 M | 15 M | 18 M | 24 M |
|---|---|---|---|---|---|---|---|---|---|---|---|
| BV-15 | 6.21 | 6.21 | 6.21 | 6.19 | 6.11 | 6.13 | 6.09 | 6.09 | 6.03 | 5.81 | 5.80 |
| BV-16 | 6.36 | 6.24 | 6.12 | 6.18 | 6.20 | 6.28 | 6.25 | 6.25 | 5.92 | 5.93 | 5.95 |
| BV-17 | 6.31 | 6.26 | 6.12 | 6.27 | 6.23 | 6.24 | 6.13 | 6.13 | 6.07 | 6.05 | 5.98 |
| BV-18 | 6.25 | 6.21 | 6.07 | 6.11 | 6.11 | 6.22 | 6.19 | 6.21 | 6.23 | 6.25 | 6.13 |

TABLE 3(i)

Rotavirus Vaccine Formulation Stability at 25° C. with CAB Buffers (FIG. 4). Stability at 25° C.

| B. No | 0 Day | 2 wk | 4 wk | 6 wk | 8 wk | 10 wk | 12 wk | 16 wk | 24 wk |
|---|---|---|---|---|---|---|---|---|---|
| BV-15 | 6.30 | 6.21 | 5.86 | 5.91 | 5.87 | 5.81 | 5.73 | 5.68 | 5.06 |
| BV-16 | 6.36 | 6.26 | 6.09 | 6.07 | 6.01 | 6.04 | 5.97 | 5.83 | 5.22 |
| BV-17 | 6.31 | 6.24 | 6.13 | 6.05 | 6.05 | 6.03 | 5.96 | 5.96 | 5.41 |
| BV-18 | 6.25 | 6.24 | 6.14 | 6.11 | 6.01 | 6.01 | 5.98 | 5.98 | 5.75 |

Example 3.4: Vaccine Formulations with 0.1M Magnesium Hydroxide Carbonate Buffer (MHC Buffer)

Magnesium Hydorxide Carbonate Dihydrate (Molecular Weight of 314.98 gm) was sequentially added to 500 ml water for injection in a sterile glass bottle so as to achieve 0.1M of Magnesium Hydroxide Carbonate. The components were shaked well for homogeneity, since this salt is water insoluble. The suspension was made to a volume of 1 liter with Water for Injection. dissolved completely and the volume was made up to 1 liter with WFI (water for injection). pH was checked and maintained to a level between 10 to 10.5. The solution was sterilized by autoclaving at 121° C. for 30 minutes. The buffer was collected into another sterile bottle and the bottle was labeled and stored at 2-8° C. for future use.

Formulations using this 0.1M Magnesium Hydroxide Carbonate buffer combination system were prepared including Rotavirus antigen 116E at $10^6$ ffu/dose and other stabilizers and components as mentioned below at dose volumes as mentioned in the following table corresponding to each formulation (identified by unique formulation numbers as mentioned in Table 3(j)), and stability of the vaccine formulation at 2° to 8° C., and 25° C. was tested at various time intervals till 2 years approximately which is given in the accompanying graph (FIG. 9).

TABLE 3(j)

Rotavirus Vaccine Formulations with MHC Buffers.

| Formulation No. | Dose volume | Formulation details | Buffer used |
|---|---|---|---|
| BV-19 | 1 ml | Sucrose 40%, Trehalose 0.5%, HSA 0.35%, LAH 1% | 0.1M Magnesium Hydroxide Carbonate Buffer |

TABLE 3(k)

Rotavirus Vaccine Formulation Stability at 2-8° C. and 25° C. with MHC Buffers (FIG. 5). Stability at 2-8° C. and 25° C.

| Temperature | 0 Day | 1 M | 4 M | 6 M | 12 M | 18 M | 24 M |
|---|---|---|---|---|---|---|---|
| 25 Deg C. | 6.75 | 6.03 | 5.31 | 4.24 | — | — | — |
| 2-8 Deg C. | 6.75 | 6.61 | 6.45 | 6.47 | 6.39 | 6.34 | 6.28 |

Example 3.5: Vaccine Formulations with 0.5M Mixed Buffer with Ammonium Salts (Mixed Buffer)

Di Ammonium hydrogen ortho phosphate (Mol Wt. 132.06 gm) to an amount of 66.03 gm, Ammonium acetate (Mol Wt. 77.08 gm) to an amount of 38.54 gm and Ammonium bicarbonate (Mol Wt. 79.02 gm) to an amount of 39.51 was added to 500 ml water for injection in a sterile glass bottle so as to achieve 0.5 M of the mixed buffer with the ammonium salts. The components were dissolved completely and the volume was made up to 1 liter with WFI (water for injection). pH was checked and maintained to a level between 7.6 and 7.8. The buffer vessel was then transferred into 2 L Stainless Steel pressure vessel and connected with filter. The solution was filtered through 0.2μ filter under Biosafety Cabinet by using compressed air. The buffer was collected into another sterile bottle and the bottle was labeled and stored at 2-8° C. for future use.

Formulations using this 0.5 M of Mixed buffer combination system were prepared including Rotavirus antigen 116E at $10^6$ ffu/dose and other stabilizers and components as mentioned below at dose volumes as mentioned in the following table corresponding to each formulation (identified by unique formulation numbers as mentioned in Table 3(l)), and stability of the vaccine formulation at 2° to 8° C., was tested at various time for a period of 1 year which is given in the accompanying graphs (FIGS. 10 to 13).

TABLE 3(l)

Rotavirus Vaccine Formulations with Mixed Buffers (Ammonium acetate + ammonium bicarbonate + Di ammonium ortho phosphate) 0.5M

| Formulation Example No. | Dose Vol. | Formulation Details | | Buffer used. |
|---|---|---|---|---|
| BV-20 | 1 ml | 10^6.0 ml/1.0 ml (Double concentration of sugars) | | 0.5M Mixed buffer |
| | | Sucrose | 40.0% | |
| | | Trehalose | 0.5% | |
| | | Lactose | 5.0% | |
| | | LAH | 0.5% | |
| | | rHSA | 0.08% | |
| BV-21 | 1.5 ml | 10^6.0/1.5 ml (Components have been calculated for 1.5 ml) | | 0.5M Mixed buffer |
| | | Sucrose | 30.0% | |
| | | Trehalose | 2.0% | |
| | | Lactose | 5.0% | |
| | | rHSA | 0.08% | |
| | | LAH | 1.0% | |

TABLE 3(m)

Rotavirus Vaccine Formulation Stability at 2-8° C. with Mixed Buffers (FIG. 6). Stability at 2-8° C. Stability of BV 9 and BV 10 at 2-8 Deg C.

| B. No | 0 Day | 1 M | 3 M | 6 M | 9 M | 12 M |
|---|---|---|---|---|---|---|
| BV-20 | 6.12 | 6.17 | 6.07 | 6.03 | 6.08 | 6.11 |
| BV-21 | 6.23 | 6.25 | 6.25 | 6.18 | 6.21 | 6.23 |

Example 4: pH Values of Buffers and Vaccine Formulations Before and after Formulations after Stability Period It is also important to check the pH of the buffers used in different formulations and the corresponding pH values while the buffers are present in the final vaccine formulations. This is to check the given pH ranges of the final vaccine formulation during and after storage period of the vaccine. Such data is presented below. The bicarbonate based systems are above pH 8, which is above the physiological buffer pH. However, the vaccine is stable even over 2 years at 2-8 Deg C. after stability period.

TABLE 3(n)

Buffer pH and vaccine pH before and after formulations at 0 day and 24 months.

| Formulation Example Number | Buffer used | Buffer pH | Vaccine pH at 0 day | Vaccine pH after 24 months |
|---|---|---|---|---|
| BV-12 | 0.03M Trisodium Citrate and 0.3M Sodium Bicarbonate Buffer Combination system | 8.21 | 7.61 | 7.82 |
| BV-15 | 0.2M Sodium Carbonate and 0.2M Sodium Bicarbonate Buffer Combination System | 9.51 | 8.71 | 8.98 |
| BV-19 | 0.3M Magnesium Hydroxide Carbonate Buffer System | 10.1 | 7.98 | 8.01 |
| BV-21 | 0.5M (Ammonium acetate + Ammonium bicarbonate + Di ammonium ortho phosphate) mixed buffer | 7.78 | 7.62 | 7.81 |

Further, experiments were conducted with fixed formulation components while changing the various buffers, and the stability of the vaccine formulations were studied over prolonged periods of time. Corresponding FIGS. 13 and 14 shows comparative vaccine stability with various novel buffers and fixed formulation components which include sucrose 40% w/v, trehalose 0.5% w/v, LAH 1% w/v, rHSA 0.35% w/v and rotavirus antigen 116E.

REFERENCES

1. Wainwright, W H. The Development of Live, Attenuated Rotavirus Vaccines: A Manufacturer's Resource Guide. Seattle:PATH; 2006.
2. Bharat Biotech's International PCT publication WO2007/132480 (granted Indian Patent 242868 and granted in UK 0821386.0) and WO2011/07363.
3. U.S. Pat. No. 6,403,098 (Merck) and U.S. Pat. No. 6,616,931 (Merck).
4. Inge Erk et. al Journal of Virology, Vol. 77, No. 6 Mar. 2003, p. 3595-3601.
5. www.ou.edu/research/electron/bmz5364/buffers.html visited Feb. 10, 2012.
6. www.nature.berkeley.edu/soilmicro/methods/phosphate%20buffer.pdf visited Feb. 10, 2012.
7. Guidelines to assure the quality, safety and efficacy of live attenuated rotavirus vaccines (oral) WHO Technical Report Series No 941, 2007.
8. Harry B. Greenberg, Mary K. Estes, Rotaviruses: From Pathogenesis to Vaccination, doi:10.1053/j.gastro.2009.02.076. (Gastroenterology 2009).
8. Penelope H. Dennehy, Rotavirus Vaccines: an Overview, Clinical Microbiology Reviews, January 2008, Vol. 21, No. 1, p. 198-208.
9. Bresee J S, Glass R I, Ivanoff B, Gentsch J. Current status and future priorities for rotavirus vaccine development, evaluation and implementation in developing countries. Vaccine 1999; 17:2207-22.
10. (Ref:Geigy scientific Tables, Volume 1, 1981 addition, Page 126).

We claim:

1. A liquid vaccine formulation comprising:
   a rotavirus antigen of strain 116E; and
   a combination buffer system, wherein the combination buffer system is a mixed buffer system comprising ammonium acetate, ammonium bicarbonate and di-ammonium orthophosphate buffer.

2. The vaccine formulation of claim 1, wherein the mixed buffer is present at a concentration range of 0.01 M to 2 M.

3. The vaccine formulation of claim 2, wherein the mixed buffer is present at a concentration of 0.5 M.

4. The vaccine formulation of claim 1, wherein the dose volume is 1 ml, which is sufficient to neutralize the acidity of the gastric environment, wherein said vaccine formulation is capable of eliciting protective immune response against infections caused by rotavirus infections.

5. The vaccine formulation of claim 1, wherein the formulation is stable for at least two years at 2°-8° C.

6. The vaccine formulation of claim 1, wherein the formulation is stable for at least 6 months at 25° C.

7. The vaccine formulation of claim 1, further comprising a sugar.

8. The vaccine formulation of claim 7, wherein the sugar comprises from 20% to 75% sucrose.

9. The vaccine formulation of claim 7, wherein the sugar comprises up to 10% lactose.

10. The vaccine formulation of claim 7, wherein the sugar comprises up to 1% trehalose.

11. The vaccine formulation of claim 1, further comprising an albumin.

12. The vaccine formulation of claim 7, wherein the albumin comprises human serum albumin.

13. The vaccine formulation of claim 7, wherein the albumin comprises up to 10% lactalbumin hydrolysate.

14. A liquid vaccine formulation comprising:
    a rotavirus antigen; and
    a buffer comprising ammonium acetate, ammonium bicarbonate, and di-ammonium orthophosphate buffer.

15. The vaccine formulation of claim 14, wherein the rotavirus antigen comprises an antigen of rotavirus strain 116E.

16. The vaccine formulation of claim 14, wherein the buffer comprises a concentration of from 0.01 M to 2 M.

17. The vaccine formulation of claim 14, wherein the buffer comprises a concentration of about 0.5M.

18. The vaccine formulation of claim 14, which has a pH from 7 to 8.5.

19. The vaccine formulation of claim 14, which is stable for at least two years at 2°-8° C.

20. The vaccine formulation of claim 14, which is stable for at least 6 months at 25° C.

21. A liquid vaccine formulation comprising:
    a rotavirus antigen; and
    a magnesium hydroxide carbonate buffer system, wherein the vaccine has a pH from 10 to 10.5.

22. The vaccine formulation of claim 21, wherein the rotavirus antigen comprises an antigen of rotavirus strain 116E.

23. The vaccine formulation of claim 21, wherein the buffer system comprises magnesium hydroxide carbonate dihydrate at a concentration of from 0.01 M to 0.5 M.

24. The vaccine formulation of claim 21, wherein the buffer system comprises magnesium hydroxide carbonate dihydrate at a concentration of about 0.1M.

25. The vaccine formulation of claim 21, which is stable for at least two years at 2°-8° C.

26. The vaccine formulation of claim 21, which is stable for at least 6 months at 25° C.

27. The vaccine formulation of claim 1, which comprises a dose volume of between 0.5 ml to 2.0 ml.

28. The vaccine formulation of claim 27, wherein the dose volume is 1.0 ml.

29. The vaccine formulation of claim 27, wherein the dose volume is 2.0 ml.

30. The vaccine formulation of claim 1, which comprises a dose volume sufficient to neutralize the acidity of the gastric environment.

31. The vaccine formulation of claim 1, which is capable of eliciting a protective immune response against infections caused by rotavirus.

32. The vaccine formulation of claim 14, which comprises a dose volume of between 0.5 ml to 2.0 ml.

33. The vaccine formulation of claim 32, wherein the dose volume is 1.0 ml.

34. The vaccine formulation of claim 32, wherein the dose volume is 2.0 ml.

35. The vaccine formulation of claim 14, which comprises a dose volume sufficient to neutralize the acidity of the gastric environment.

36. The vaccine formulation of claim 14, which is capable of eliciting a protective immune response against infections caused by rotavirus.

37. The vaccine formulation of claim 21, which comprises a dose volume of between 0.5 ml to 2.0 ml.

38. The vaccine formulation of claim 37, wherein the dose volume is 1.0 ml.

39. The vaccine formulation of claim 37, wherein the dose volume is 2.0 ml.

40. The vaccine formulation of claim 21, which comprises a dose volume sufficient to neutralize the acidity of the gastric environment.

41. The vaccine formulation of claim 21, which is capable of eliciting a protective immune response against infections caused by rotavirus.

* * * * *